US007966072B2

(12) United States Patent
Yun et al.

(10) Patent No.: US 7,966,072 B2
(45) Date of Patent: Jun. 21, 2011

(54) METHODS AND COMPOSITIONS FOR TREATING OBESITY-HYPOVENTILATION SYNDROME

(75) Inventors: Anthony Joonkyoo Yun, Palo Alto, CA (US); Patrick Yuarn-Bor Lee, Menlo Park, CA (US)

(73) Assignee: Palo Alto Investors, Palo Alto, CA (US)

( * ) Notice: Subject to any disclaimer, the term of this patent is extended or adjusted under 35 U.S.C. 154(b) by 631 days.

(21) Appl. No.: 11/344,586

(22) Filed: Jan. 30, 2006

(65) Prior Publication Data
US 2006/0190052 A1 Aug. 24, 2006

Related U.S. Application Data

(60) Provisional application No. 60/654,139, filed on Feb. 18, 2005.

(51) Int. Cl.
*A61N 1/36* (2006.01)
(52) U.S. Cl. ......................................................... 607/42
(58) Field of Classification Search ................ 607/42
See application file for complete search history.

(56) References Cited

U.S. PATENT DOCUMENTS

| 4,830,008 | A | * | 5/1989 | Meer | 607/42 |
| 5,146,918 | A | * | 9/1992 | Kallok et al. | 607/2 |
| 5,472,438 | A | | 12/1995 | Schmit et al. | |
| 5,540,733 | A | * | 7/1996 | Testerman et al. | 607/42 |
| 5,797,923 | A | | 8/1998 | Aiyar et al. | |
| 5,911,218 | A | * | 6/1999 | DiMarco | 128/200.24 |
| 6,099,479 | A | * | 8/2000 | Christopherson et al. | 600/529 |
| 6,132,384 | A | * | 10/2000 | Christopherson et al. | 600/529 |
| 6,251,126 | B1 | * | 6/2001 | Ottenhoff et al. | 607/42 |
| 6,269,269 | B1 | * | 7/2001 | Ottenhoff et al. | 607/42 |
| 6,463,327 | B1 | * | 10/2002 | Lurie et al. | 607/42 |
| 6,572,543 | B1 | * | 6/2003 | Christopherson et al. | 600/300 |
| 2005/0021102 | A1 | | 1/2005 | Ignagni et al. | |
| 2005/0085867 | A1 | * | 4/2005 | Tehrani et al. | 607/42 |

OTHER PUBLICATIONS

The Merck Manuals Online Medical Library: Home Edition for Patients and Caregivers. "Control of Breathing." 2006. <http://www.merck.com/mmhe/print/sec04/ch038/ch038e.html>.*
"Obesity Hypoventilation Syndrome." MedlinePlus Medical Encylopedia Online. MedlinePlus Medical Encyclopedia, 2009. Web. Mar. 17, 2010.*
"Central Sleep Apnea." MedlinePlus Medical Encylopedia Online. MedlinePlus Medical Encyclopedia, 2009. Web. Mar. 17, 2010.*

* cited by examiner

*Primary Examiner* — Carl H Layno
*Assistant Examiner* — Gary A Porter, Jr.
(74) *Attorney, Agent, or Firm* — Bozicevic, Field & Francis LLP; Bret E. Field; Lynn J. Kidder

(57) ABSTRACT

Methods and compositions for treating a subject for obesity-hypoventilation syndrome, or related conditions, are provided. The subject methods include applying an electrical stimulus to a subject in a manner that modulates chest cavity capacity in a manner effective to treat the subject. Also provided are compositions, kits and systems for use in practicing the subject methods.

9 Claims, 1 Drawing Sheet

US 7,966,072 B2

METHODS AND COMPOSITIONS FOR TREATING OBESITY-HYPOVENTILATION SYNDROME

CROSS-REFERENCE TO RELATED APPLICATIONS

Pursuant to 35 U.S.C. §119 (e), this application claims priority to the filing date of U.S. Provisional Patent Application Ser. No. 60/654,139 filed Feb. 18, 2005; the disclosure of which application is herein incorporated by reference.

INTRODUCTION

1. Background of the Invention

Obesity-hypoventilation syndrome (OHS), also known as Pickwickian syndrome, is a under-recognized condition related to, but potentially occurring separately from, obstructive sleep apnea. In OHS, an obese individual does not breathe enough oxygen while asleep or awake. The cause of OHS is unknown, but is thought to potentially involve problems in mobilizing the chest wall and diaphragm effectively to produce effective air exchange. Consequently, blood remains low in oxygen and high in carbon dioxide. Lack of sleep, poor quality of sleep, and lack of sufficient oxygen leads to chronic fatigue. As a consequence of obesity, OHS is likely yet another manifestation of the constellation of metabolic disorders known as syndrome X.

Currently, the treatment of OHS involves mechanical ventilation to help the person breath. Specific options include: non-invasive mechanical ventilation (BiPAP or other modes) through a mask that fits tightly over the nose or nose and mouth and mechanical ventilation through a tracheostomy. Other therapies are aimed at weight loss, which may lead to reversal of the OHS. Such treatment approaches are not entirely satisfactory.

Given the demographic trends towards the increasing prevalence of obesity in the population, OHS looks to significantly increase in incidence over time. As such, there is a continued need for the development of new OHS treatment protocols.

2. Relevant Literature

United States Published Patent Application 20050021102 and Issued U.S. Pat. Nos. 5,797,923 and 5,472,438.

SUMMARY

Methods and compositions for treating a subject for obesity-hypoventilation syndrome are provided. The subject methods include applying an electrical stimulus to a subject to modulate chest cavity capacity in a manner effective to treat the subject. Also provided are compositions, kits and systems for use in practicing the subject methods.

DEFINITIONS

Figure 1:
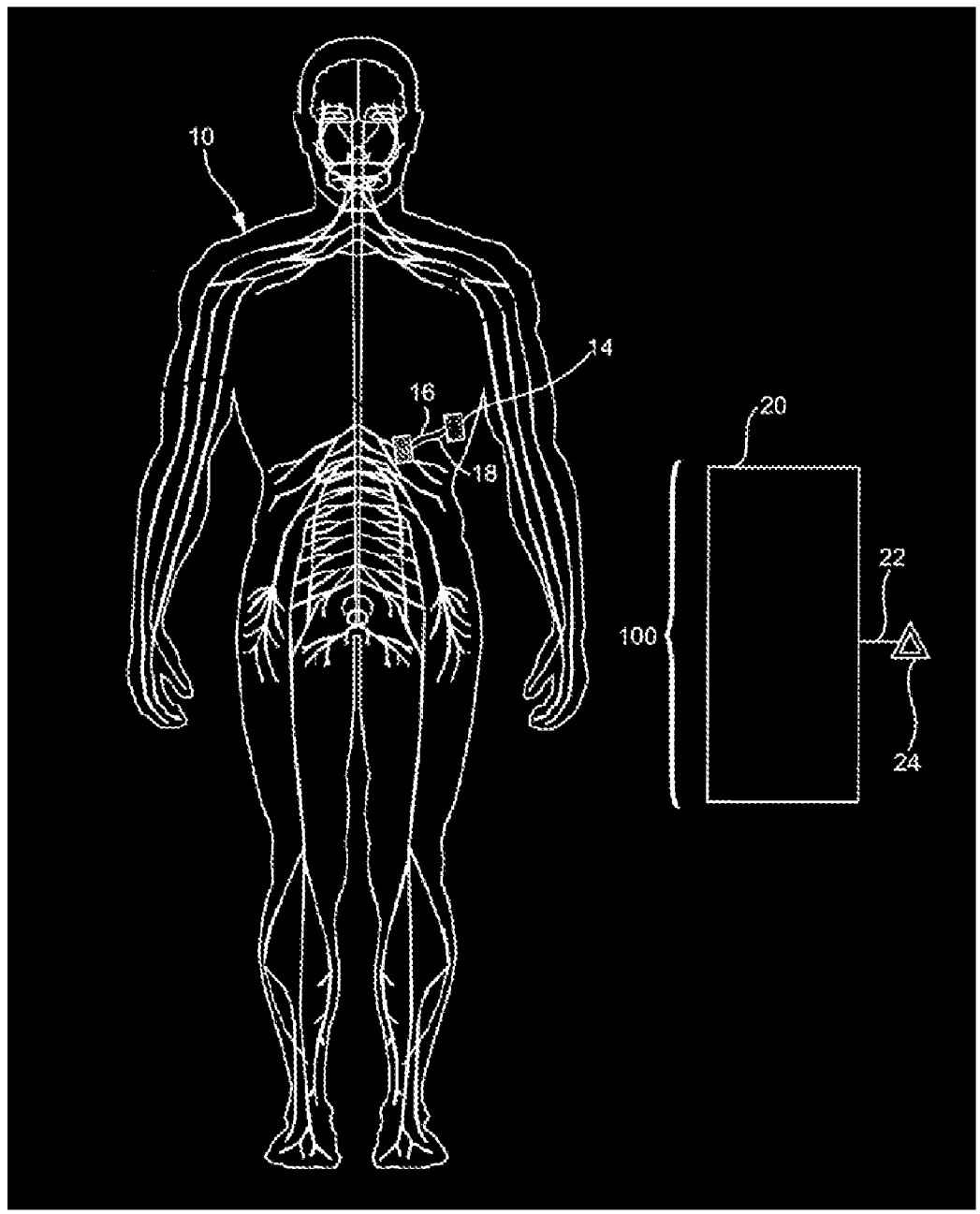
FIG. 1 shows an exemplary embodiment of an electro-stimulatory device operatively positioned in a subject's body in accordance with the subject methods.

The following includes definitions of selected terms used throughout the disclosure. The definitions include examples of various embodiments and/or forms of components that fall within the scope of a term and that may be used for implementation. Of course, the examples are not intended to be limiting and other embodiments may be implemented. Both singular and plural forms of all terms fall within each meaning:

"Patient," as used herein, includes but is not limited to any living creature, i.e. human or animal, also referred to herein as a subject.

"Signal", as used herein, includes but is not limited to one or more electrical signals, AC or DC, analog or digital signals, one or more computer or processor instructions, or other means that can be received, transmitted, and/or detected.

The term "electrical stimulus" is used broadly to refer to any application of electrical energy to tissue, where the application of electrical energy may result in an enhancement or stimulation of a biological process, e.g., muscle contraction, or an inhibition of a biological process, e.g., muscle contraction.

"Software", as used herein, includes but is not limited to one or more computer readable and/or executable instructions that cause a computer or other electronic device to perform functions, actions, and/or behave in a desired manner. The instructions may be embodied in various forms such as objects, routines, algorithms, modules or programs including separate applications or code from dynamically linked libraries. Software may also be implemented in various forms such as a stand-alone program, a function call, a servlet, an applet, instructions stored in a memory, part of an operating system or other type of executable instructions. It will be appreciated by one of ordinary skill in the art that the form of software may be dependent on, for example, requirements of a desired application, the environment it runs on, and/or the desires of a designer/programmer or the like. It will also be appreciated that computer-readable and/or executable instructions can be located in one logic and/or distributed between two or more communicating, co-operating, and/or parallel processing logics and thus can be loaded and/or executed in serial, parallel, massively parallel and other manners.

Electrical stimulation can have one or more of the following effects: 1) eliciting muscle fiber type conversion (from fast twitch, rapidly fatiguing, type I fibers to slow twitch, slowly fatiguing type II fibers); 2) increasing muscle mass (through reversal of disuse atrophy); 3) changing the contractile properties of the muscle by stimulating through the muscle's range of motion (thereby reducing any shortening of fibers and/or spasticity), and 4) even potentially having an effect of collateral sprouting of adjacent nerve fibers to innervate muscle that has lost its innervation through damage to the phrenic nerve or lower motor neuron.

DETAILED DESCRIPTION

Methods and compositions for treating a subject for obesity-hypoventilation syndrome are provided. The subject methods include applying an electrical stimulus to a subject to modulate chest cavity capacity in a manner effective to treat the subject. Also provided are compositions, kits and systems for use in practicing the subject methods.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

All patents, patent applications and publications mentioned herein are incorporated herein by reference to disclose and describe the methods and/or materials in connection with which the patents, patent applications and publications are cited. The citation of any patent, patent application and publication is for its disclosure prior to the filing date and should not be construed as an admission that the present invention is not entitled to antedate such patent, patent application and publication by virtue of prior invention. Further, the dates of publication provided may be different from the actual publication dates which may need to be independently confirmed.

It must be noted that as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention.

The Figures shown herein are not necessarily drawn to scale, with some components and features being exaggerated for clarity.

Accordingly, it is a principal object and advantage of the current invention to provide a unique solution to the issue of OHS. Patient suffering from this syndrome typically are either subjected to measures for sleep apnea resulting from physical obstruction of the upper airway or to measures that address presumed central neurologic dysfunction. All current measures fail to recognize the inherent limitation placed upon the function of respiration by a chest cavity trammeled by excess surrounding mass.

As summarized above, aspects of the invention provide methods of treating a subject for obesity-hypoventilation syndrome. The subject methods can, furthermore, be used to treat comorbid manifestations of syndrome X, such as diabetes mellitus, hypertension, and hyperlipidemia. The methods can include the steps of implanting an electrode adjacent to a target site in the diaphragm of the patient and operating the electrode to deliver a sufficient amount of electrical stimulation to the target site in the diaphragm of the patient to cause the diaphragm to contract more vigorously, thereby overcoming the issue of lung compression by excess fat below the diaphragm. Alternatively, or in addition, the methods can include the steps of implanting an electrode adjacent to a target site in the diaphragm of the patient and operating the electrode to deliver a sufficient electrical signal to inhibit native electrical stimulation of the diaphragm to cause the diaphragm to relax to a greater extent, thereby enhancing lung compression by excess fat below the diaphragm. Alternatively, or in addition, the methods can include the steps of implanting an electrode adjacent to a target site in the chest wall of the patient and operating the electrode to deliver a sufficient amount of electrical stimulation to chest wall muscles to cause the chest wall muscles to contract more vigorously, thereby overcoming the issue of chest wall movement compromise by excess fat in the chest wall. Alternatively, or in addition, the methods can include the steps of implanting an electrode adjacent to a target site in the chest wall of the patient and operating the electrode to deliver a sufficient electrical signal to inhibit native electrical stimulation of chest wall muscles to cause the chest wall muscles to relax more extensively, thereby harnessing chest wall movement compromise by excess fat in the chest wall to further reduce the size of the chest cavity. A method for coordinated stimulation/inhibition of both diaphragm and chest wall muscles to effect maximum dynamic range of lung inflation and deflation is specifically described.

Representative embodiments include an apparatus, e.g., system, and method for treating OHS, as well as for preventing its onset in patients at risk. A system and method is provided for electrically stimulating/inhibiting the diaphragm of a patient to effect expansion of the chest cavity. A second system and method is provided for electrically stimulating/inhibiting the chest wall muscles of a patient to effect expansion of the chest cavity. The two methods may be coordinated such that contraction and relaxation of both diaphragm and chest wall muscles occurs in a pattern such that the chest cavity dimensions achieves maximum possible expansion. Delivery of electrical energy to the diaphragm and/or chest wall muscles may also have one or more of the following effects: eliciting muscle fiber type conversion, increasing muscle mass, changing the contractile proportions of the muscle, and stimulating collateral innervation.

One aspect of representative embodiments may include an electrical signal generator and electrodes implanted into the diaphragm of the patient to apply electrical stimulation/inhibition to the diaphragm of the patient.

One aspect of representative embodiments may include an electrical signal generator and electrodes implanted into the chest wall muscles of the patient to apply electrical stimulation/inhibition to the chest wall muscles.

In one embodiment, the electrical signal generator can be configured to generate pulses and or signals that may take the form of sinusoidal, stepped, and trapezoidal waveforms, or other relatively continuous signals. The electric signal generator can include one or more channels that can independently control the amplitude, frequency, timing and pulse width of the corresponding electrodes connected thereto.

In one embodiment, the electrical signal generator can be an external signal generator that is electrically connected to or in electrical communication with the electrodes. One example of a suitable electrical signal generator is the NeuRx RA/4 stimulator that is manufactured by Synapse Biomedical, Inc., of Oberlin, Ohio. The NeuRx RA/4 stimulator is a four-channel device with independent parameter programmability. It will be appreciated that since the NeurRx/4 stimulator has four channels, it has the capability to independently control up to four electrodes, ideal for an embodiment such as that described above where stimulation/inhibition of separate groups of muscles is critical for effective deployment of the method. In an alternative embodiment, the electrical signal generator can be an implantable signal generator. One suitable example of a fully implanted signal generator is the "ITREL II" electrical signal generator available from Medtronic, Inc. of Minneapolis, Minn. One example of a partially implanted radiofrequency signal generator system is the "XTREL" system available from Medtronic, Inc. of Minneapolis, Minn.

As stated above, the system can include electrodes implanted in the diaphragm and/or chest wall muscles of the patient to provide electrical stimulation/inhibition. One or more electrodes can be used to provide sufficient electrical stimulation/inhibition.

The electrode can be an intramuscular electrode that is configured to be implanted into the muscle tissue of the patient. One example of a suitable intramuscular electrode is the Peterson intramuscular electrode manufactured by Synapse Biomedical, Inc., of Oberlin, Ohio. In one configuration, the Peterson intramuscular electrode is a double helix wound from multistrand stainless steel wire insulated in fluoropolymer with a polypropylene core and barb. The electrode can have a barb that is flattened and bent back along the line of the electrode, a polypropylene skirt and a deinsulated coil under the skirt. The electrode lead can terminate with a stainless steel pin crimped to the de-insulated end and backfilled with silicone adhesive for strain relief. It will be appreciated that the intramuscular electrode can take the form of other shapes, sizes, and configurations, and can be made of other materials suitable for implantation into a patient.

In one embodiment, the electrodes can be implanted into target sites in the diaphragm and/or the chest wall muscles of the patient. The target sites can be adjacent to the point of termination of the corresponding afferent motor nerve supply for the muscle in question.

In one embodiment, an electrode can be implanted into or adjacent to the point of termination of the corresponding afferent motor nerve supply for the muscle in question, and an additional electrode can be implanted in each hemidiaphragm for one or more of the following reasons: to backup the primary electrode, to gain higher output if the primary electrode is imprecisely located, or to allow for surgical error in placement.

In one embodiment, the system can include an indifferent electrode. The indifferent electrode can be similar to the intramuscular electrodes show and described above, except that it has a shorter de-insulated tip and does not have a barb at one end. In one embodiment, the indifferent electrode can be used as a common anode that can provide a return for the electrical charge from the electrodes. One suitable example of an indifferent electrode is PN 21-0004 manufactured by Synapse Biomedical, Inc. It will be appreciated that other indifferent electrodes can take the form of other shapes, sizes, and configurations, and can be made of other materials suitable for implantation into a patient or placed on the skin surface.

In one embodiment, the indifferent electrode can be implanted in the subcutaneous tissue adjacent to the musculature in question. Alternatively, the indifferent electrode can be implanted in other areas such as integral to an implanted pulse generator or on the skin surface.

In one embodiment, the electrical signal generator can supply the electrodes with an electrical signal that serves as electrical stimulation/inhibition.

In one embodiment, the electrical stimulation/inhibition can be delivered to the diaphragm and/or the chest wall muscles continuously or periodically. All relevant sets of muscles can be stimulated continuously, or some can be stimulated continuously and others periodically, or all periodically, depending on the needs of a particular patient.

In one embodiment, the electrodes can be implanted into the diaphragm and/or chest wall muscles via a minimally invasive technique.

In one embodiment, the electrodes can be implanted into the diaphragm and/or chest wall muscles via an open surgical technique and specific placement with a hypodermic needle.

In one embodiment, the system can include a stimulation/inhibition apparatus that can include an electrical signal generator and a breathing sensor and control circuit that is in electrical communication with the electrical signal generator and the flow sensor. The breathing sensor and control circuit can be configured to detect certain breathing attributes of the patient, convert these attributes to signals, and communicate these signals to the electrical signal generator. Such attributes can include, but are not limited to, the inspiration phase of a breath, the duration of the inspiration phase, the exhalation phase of a breath, the duration of the exhalation phase, tidal volume, and flow rate.

In one embodiment, the system can include a pressure gauge and gas meter to measure the pressure and gas related parameters of the patient's breathing.

In one embodiment, the system can include a physiological measurement unit to measure items such as blood pressure, blood chemistry value, body temperature, and other relevant parameters.

In one embodiment, electrical stimulation/inhibition of the diaphragm and/or chest wall muscles can be synchronized with the patient's own attempts at breathing, successful or not. For example, electrical stimulation can be triggered following the inspiration phase of the breath to maximize contraction at the time of longest length. It will be appreciated that electrical stimulation of the diaphragm and/or chest wall muscles may not be synchronized with the patient's own attempts at breathing, successful or not, and thus can be applied during any portion of a breath.

In certain embodiments, the methods further include the step of diagnosing the presence of OHS in the subject. The main symptoms of OHS are due to sleep deprivation, which results from sleep loss and poor sleep quality (see obstructive sleep apnea). Such symptoms include: Excessive daytime sleepiness; Falling asleep at inappropriate times during the day; Increased risk for accidents or errors at work and Depression. In addition, symptoms of chronic hypoxia (low blood oxygen level) can also occur, such as shortness of breath or fatigue after minimal physical effort. Diagnosis can include performing one or more tests. Persons with OHS are usually very overweight. Physical signs that suggest OHS include: Cyanosis (bluish coloration of the lips, fingers, toes, or skin); Signs of right heart failure (corpulmonale), including: Swollen legs or feet, Shortness of breath or easy fatigue on minimal effort. Tests done to confirm the diagnosis may include: Arterial blood gas, Sleep study, Pulmonary function.

A number of different devices may be employed in accordance with the subject invention. For example, device and systems for applying electrical energy to a subject and which may be adapted for use in the subject invention are described, e.g., in copending U.S. patent application Ser. Nos. 10/661,368, 10/871,366 and elsewhere, the disclosures of the US patent applications are herein incorporated by reference. Such devices may be positioned directly on a targeted area, e.g., positioned below the skin of a subject directly on or adjacent a portion of the nervous system (e.g., one or more nerve fibers) such as an implantable device, or may be an external device (i.e., some or all of the device may be external to the subject). In accordance with the subject invention, one or more electrodes or electrical contacts may be positioned directly on or adjacent a targeted area, where the one or more electrodes may be surgically implanted, e.g., directly on or adjacent a targeted nerve fiber of a subject. In certain embodiments, an immunomodulator such as a steroid or the like, may be incorporated into a surface contacting area of a device, e.g., to minimize inflammation of the targeted site.

An electric energy applying device typically includes a stimulator such as an electrode, a controller or programmer and one or more connectors for connecting the stimulating device to the controller. In certain embodiments more than one electrode may be employed. In further describing representative electrodes, such are described in the singular, but it will be apparent that more than one electrode may be used, where such may be the same or may be different in one or more aspects. Accordingly, the description of an exemplary electrode suitable for use in the subject methods is applicable to other electrodes that may be employed. The electrode employed in the subject invention is controllable to provide output signals that may be varied in voltage, frequency, pulse width, current and intensity. The electrode may be one that provides both positive and negative current flow from the electrode and/or may be capable of stopping current flow from the electrode and/or changing the direction of current flow from the electrode. For example, embodiments include an electrode that is controllable in these respects, i.e., controllable in regards to producing positive and negative current flow from the electrode, stop current flow from the electrode, change direction of current flow from the electrode, and the like. In certain embodiments, the electrode has the capacity for variable output, linear output and short pulse width.

FIG. 1 shows an embodiment of an electrostimulatory device 100. Device 100 may be implanted, for example, in a target site in the diaphragm, or in the chest wall of a subject's body 10. One or more leads 23 are shown positioned to electrically stimulate and/or inhibit activity in one or more areas of the chest cavity. Device 100 includes energy source 14 which may take the form of a modified signal generator, for example such as those manufactured by Medtronic, Inc. under the trademark INTREL II. Lead 23 may take the form of any suitable lead, such as any of the leads that are sold with the Medtronic device and is coupled to energy source 14 by one or more conventional conductors 16 and 18.

The energy source 14 for the electrical output may be provided by a battery or generator such as a pulse generator that is operatively connected to the electrode. Device 100 which includes energy source 14 may be positioned in any suitable location such as adjacent to the electrode (e.g., implanted adjacent the electrode), or a remote site in or on the subject's body or away from the subject's body in a remote location and the electrode may then be connected to the remotely positioned energy source using wires, e.g., may be implanted at a site remote from the electrode or positioned outside the subject's body in certain instances. Of interest are implantable generators analogous to a cardiac pacemaker. In addition, of interest are implantable devices capable of generating power from the endogenous thermodynamic and electric energy of the body.

The electrode may be mono-polar, bipolar or multi-polar. In order to minimize the risk of an immune response triggered by the subject against the device and minimize damage such as corrosion and the like to the device from other biological fluids, etc., the electrode and any wires and optional housing materials are made of inert materials such as for example silicon, metal, plastic and the like. For example, a multi-polar electrode having about four exposed contacts (e.g., cylindrical contacts) may be employed.

A controller or programmer 20 may also be coupled with an electric energy applying device. The programmer is typically one or more microprocessors under the control of a suitable software program. Other components of the programmer will be apparent to those of skill in the art, e.g., analog to digital converter, etc. The electric energy applying device may be pre-programmed for desired parameters. In certain embodiments the parameters are controllable such that the electrode signal may be remotely modulated to desired settings without removal of the electrode from its targeted position. Remote control may be performed, e.g., using conventional telemetry with an implanted electric signal generator and battery, with an implanted radiofrequency receiver 24 connected via conductor 22 coupled to an external transmitter, and the like. In certain embodiments, some or all parameters of the electrode may be controllable by the subject, e.g., without supervision by a physician. For example, a magnetic signal may be employed. In such embodiments, one or more magnets may be employed such that upon bringing a magnet in proximity to or away from the power source such as a pulse generator, the magnet may be employed to interfere with the electronic circuitry thus modulating the power—either increasing or decreasing the power supplied depending on whether the magnet is brought in proximity or moved away from the power source.

The lead may include a paddle lead, a lead having one or more electrodes and/or catheters, or a combination catheter/lead capable of providing electrical impulses and pharmacological delivery. In certain embodiments, a lead may be composed of concentric tubes such as made of platinum or other like material. The tubes may be coated with a polymer except for the distal portions that may serve as the electrodes. Conductive wires carrying energy to the electrodes may be in the interior of the concentric tubes. Optionally, a distal electrode end may include a small recording microelectrode to help assist in the actual placement of the lead.

The present invention may be operated as an open-loop controlled system. In an open-loop system, the physician or patient may at any time manually or by the use of pumps or motorized elements adjust treatment parameters such as pulse amplitude, pulse width, pulse frequency, or duty cycle. Optionally, the present invention may incorporate a closed-loop control system which may automatically adjust the electrical parameters in response to a sensed parameter or condition of a subject. Under a closed-loop feedback system to provide automatic adjustment of parameters of the electrodes, a sensor that senses a condition of the body is utilized. More detailed descriptions of sensors that may be employed in the practice of the subject invention, and other examples of sensors and feedback control techniques that may be employed are disclosed in U.S. Pat. No. 5,716,377, which is incorporated herein by reference.

Operative placement of a suitable electric energy applying device may be accomplished using any suitable technique. An electrode introducer needle may be employed to implant the electrode on or proximate to the area of interest. The size of the introducer needle may vary depending on the diameter of the electrode, etc., where in certain embodiments the electrode introducer needle may be a 12-gauge, 14-gauge, 16-gauge, 18-gauge, 20-gauge needle or 22-gauge needle, e.g., an electrode introducer needle available from Radionics in the Sluyter-Mehta kit as SMK 100 mm 2 mm active tip cannula. However, it should be understood that other electrode introducer needles may be used as appropriate to the needs and skill level of the practitioner performing the surgical procedure.

At least one imaging apparatus such as a CT scan, MRI apparatus, ultrasound apparatus, fluoroscope, or the like, may be employed to monitor the surgical. For exemplary purposes only, the subject method will be described using a fluoroscope, where such is in no way intended to limit the scope of the invention. The subject is placed in a suitable position for access e.g., supine, on a fluoroscopy table, with the patient's nose pointing vertically. The fluoroscope is then adjusted to a straight lateral position. And the entry point for the insertion of the electrode is determined.

Once the entry point is determined, the skin overlying the entry point is shaved and prepared with antiseptic solution. A 25-gauge needle may be used to inject a subcutaneous local anesthetic (such as, for example, 2 cc of 2% lidocaine) into the skin and subcutaneous tissues overlying the entry point. In addition to the local anesthetic, the patient may be given intravenous sedation and prophylactic antibiotics prior to commencement of the implantation procedure if desired. The electrode introducer needle is inserted at the entry point and advanced. The fluoroscope may be adjusted as the needle is advanced. Once the needle is positioned the stylet is withdrawn from the electrode introducer needle. Once the implanted electrode is in place, the end of the electrode that is outside the skin is carefully held in place against the skin. The electrode introducer needle may then be slowly removed, leaving the implanted electrode in place. At this point, if desired, a few small subcutaneous sutures may be placed around the electrode to hold it in the desired position.

Once the needle has been completely removed and the implanted electrode is in the final position, then the proximal part of the electrode that is coming out of the skin may be secured to the skin of the subject, e.g., by adhesive tape. Additionally, a small incision may be made on the skin at the area the electrode exits the face. Then several subcutaneous sutures may be placed around the electrode to hold it in place. The distal end of the electrode may then be connected to an extension wire or catheter, which is tunneled to the subclavicular area, or another region which will house the device used as an energy source for the implanted electrode. The device or devices used to control the electrode may be surgically implanted in the desired region by procedures known in the art, such as have been applied in surgical neuromodulation therapies used to treat Parkinson's disease. In certain embodiments of the subject invention, an electrode may be utilized which, instead of or in addition to delivering electric impulses to at least a portion of the autonomic nervous system, delivers a pharmacological agent to at least a portion of the autonomic nervous system. For example, an electrode may be used that has a small port at its tip which is connected to a reservoir or pump containing a pharmacological agent. The pharmacological agent delivery electrode may be implanted using an analogous procedure as that described above for the autonomic system modulating-electrode. In certain embodiments the reservoir or pump may also be implanted in the subject's body, analogous to that described above for the electrical impulse generator. The pharmacological agent delivery electrode may be controllable such that the amount of pharmacological agent delivered, the rate at which the pharmacological agent may be delivered, and the time period over which the pharmacological agent is delivered may be adjusted.

In embodiments in which electrical energy is used, any suitable protocol may be used, where certain protocols include using an electric energy-applying device to deliver a suitable amount of electrical energy to a subject. Once an electric energy applying device is positioned in a suitable position on or about one or more targeted areas electrical energy is applied thereto for a period of time sufficient to provide the desired effect. This period of time will vary depending on the area (e.g., the nerve fiber) being treated, the condition being treated, etc. Certain embodiments include simultaneously monitoring (i.e., in "real time") the as aspect of the nervous system such that a given nerve fiber may be electrically stimulated (or electrically inhibited) until the desired result is observed. Still further, in many embodiments once the desired result is achieved, a targeted area may be repeatedly electrically stimulated (or inhibited) one or more times to maintain the desired state such that the subject methods may be repeated one or more times, i.e., the subject methods include chronically applying electrical energy to a subject, such as chronically applying electrical energy to one or more nerve fibers. For example, in certain embodiments electrical stimulation (e.g., intermittent mild electrical pulses) may be delivered to a given area of the nervous system, twenty-four hours a day for a period of days, weeks, months, or even years in certain embodiments.

During the period of time that electrical energy is applied to a given area, the electrical energy may be substantially continuous, including continuous or intermittent (i.e., pulsed or periodic), where in many embodiments the electrical energy is in the form of electrical pulses. In other words, in certain embodiments electrical energy may be given continuously during the above-described period of time and in certain embodiments electrical energy may be given to an area in a pulsed or intermittent manner during the period of time described above. In accordance with the subject methods to apply electrical energy to a subject, once operatively positioned the electric energy applying device is activated to provide an electrical signal to the targeted area in a manner effective to practice the subject methods.

In practicing the subject methods, activation of the electric energy applying device directly applies the electrical output of the device, i.e., electrical impulses, to the targeted area. The exact parameters of the applied electrical energy may vary depending on the particular subject, condition being treated, etc. For example, an electronic current wave may be provided when the electrical energy is applied. In certain embodiments, the current wave includes current waves of high frequency, e.g., high frequency pulses, where the current wave may also include low frequency amplitude modulation. In certain embodiments, a plurality of high frequency bursts of current pulses may be applied in addition to the application of underlying low frequency continuous stimulus. Stimulation may be monopolar or multipolar. For example, to stimulate a targeted area, voltage or intensity may range from about 1 millivolt to about 1 volt or more, e.g., 0.1 volt to about 50 volts, e.g., from about 0.2 volt to about 20 volts and the frequency may range from about 1 Hz to about 2500 Hz, e.g., about 1 Hz to about 1000 Hz, e.g., from about 2 Hz to about 100 Hz in certain embodiments. In certain embodiments a pure d-c voltages may be employed. The pulse width may range from about 1 microsecond to about 2000 microseconds or more, e.g., from about 10 microseconds to about 2000 microseconds, e.g., from about 15 microseconds to about 1000 microseconds, e.g., from about 25 microseconds to about 1000 microseconds. The electrical output may be applied for at least about 1 millisecond or more, e.g., about 1 second, e.g., about several seconds, where in certain embodiments the stimulation may be applied for as long as about 1 minute or more, e.g., about several minutes or more, e.g., about 30 minutes or more may be used in certain embodiments.

In certain embodiments, a control feedback loop is provided. For example, during or following a particular electric energy applying protocol, a biological aspect of a subject may be monitored, e.g., by sensing conduction in a neuronal system, e.g., in a particular electrically stimulated nerve fiber, or by any suitable method. For example, a sensor suitable for detecting nerve cell or axon activity may be implanted in a portion of a subject's body. A sensor may take the form of an electrode or the like. Signals received by such a sensor may be amplified before further processing. A sensor may also take the form of a device capable of detecting nerve compound action potentials or may take the form of a transducer that includes an electrode with an ion selective coating applied which is capable of directly transducing the amount of a particular transmitter substance or its breakdown by-products. In utilizing a feedback system, if predetermined detection criteria are not detected, the same or a different stimulus protocol may be performed and may be automatically initiated under the control of a controller. For example, in those instances where a different protocol is performed, one or more of the electrical energy applying parameters may be modified, e.g., the pulse width may be increased, or the like, in the second protocol.

In addition to electrical energy applying devices, devices to withdraw electrical energy from the site of treatment, to create electrical current flow within the site of treatment, to create differential alignment of charge within the site of treatment, to alter the conductance/resistance characteristics of the site of treatment, as well as to impose magnetic fields upon or derive magnetic fields from the site of treatment, also are candidates for mechanisms by which to impose therapeutic interventions. As such, of interest are devices that electrically modulate the site of treatment.

Certain embodiments may entail endovascular delivery of the stimulus producing device. Other embodiments may involve laparoscopic delivery of the device; others may require surgical placement; and still others may require transcutaneous delivery of the appropriate stimulus.

Of particular interest in certain embodiments are the devices disclosed in published U.S. Patent Application No. 20050021102, the disclosure of which is herein incorporated by reference.

As reviewed above, the subject methods are directed to treating a subject for OHS. By treatment is meant that at least an amelioration of the symptoms associated with the condition afflicting the host is achieved, where amelioration is used in a broad sense to refer to at least a reduction in the magnitude of a parameter, e.g. symptom, associated with the condition being treated. As such, treatment also includes situations where the pathological condition, or at least symptoms associated therewith, are completely inhibited, e.g. prevented from happening, or stopped, e.g. terminated, such that the host no longer suffers from the condition, or at least the symptoms that characterize the condition.

A variety of hosts are treatable according to the subject methods. In certain embodiments, such hosts are "mammals" or "mammalian," where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In many embodiments, the hosts will be humans.

Computer Readable Mediums and Programming Stored Thereon

The subject invention includes computer readable media having programming stored thereon for implementing the subject methods. For example, the subject invention may include suitable computing means such as suitable hardware/software for performing the subject methods.

In certain embodiments, programming may control a device to administer a pharmacological agent to a subject, e.g., programming may be configured to determine suitable dosage, etc. In certain embodiments programming may control a device to administer electrical energy to a subject, e.g., may control the activation/termination of electrical energy including selecting suitable electrical parameters. Programming may be configured to, or otherwise be capable of, directing a microprocessor to activate, i.e., turn "on" and "off" an electric energy applying device for applying energy to a subject. For example, if so determined, the processor may direct the electric energy applying device to provide the appropriate energy to result in the desired action. Accordingly, a processor may select the appropriate parameters (e.g., frequency, amplitude, etc.) depending on what is required and direct an electric energy applying device to implement the parameters. Programming according to the subject invention may be recorded on computer-readable media, e.g., any medium that can be read and accessed directly or indirectly by a computer. Such media include, but are not limited to, computer disk or CD, a floppy disc, a magnetic "hard card", a server, magnetic tape, optical storage such as CD-ROM and DVD, electrical storage media such as RAM and ROM, and the hybrids of these categories such as magnetic/optical storage media. One of skill in the art can readily appreciate how any of the presently known computer readable mediums may be used to provide a manufacture that includes a recording of the present programming/algorithm for carrying out the above-described methodology. Thus, the computer readable media may be, for example, in the form of any of the above-described media or any other computer readable media capable of containing programming, stored electronically, magnetically, optically or by other means. As such, stored programming embodying steps for carrying-out some or all of the subject methods may be transferred to a computer-operated apparatus such as a personal computer (PC) or the like, by physical transfer of a CD, floppy disk, or like medium, or may be transferred using a computer network, server, or other interface connection, e.g., the Internet.

For example, the subject invention may include a computer readable medium that includes stored programming embodying an algorithm for carrying out the subject methods, where such an algorithm is used to direct a processor or series of processors to execute the steps necessary to perform the task (s) required of it and as such in certain embodiments the subject invention includes a computer-based system for carrying-out some or all of the subject methods. For example, such a stored algorithm may be configured to, or otherwise be capable of, directing a microprocessor to receive information directly or indirectly from data gathering means and process that information to determine if intervention is required. The result of that processing may be communicated to a user, e.g., via audio and/or visual means, e.g., the algorithm may also include steps or functions for generating a variety of profile graphs, plots, etc.

The subject invention may also include a data set of known or reference information stored on a computer readable medium to which data collected may be compared for use in determining a given treatment regimen. The data may be stored or configured in a variety of arrangements known to those of skill in the art.

Kits

Also provided are kits for practicing the subject methods. Kits may include an electric energy applying device, as described above. Devices for delivering, e.g., implanting, an electric energy applying device to a target site of a subject such as into the body cavity of a subject may also be included in the subject kits. For example, an endoscope, introducer needle, and the like may be provided.

The subject kits may also include instructions for how to practice the subject methods using the components of the kit.

The instructions may be recorded on a suitable recording medium or substrate. For example, the instructions may be printed on a substrate, such as paper or plastic, etc. As such, the instructions may be present in the kits as a package insert, in the labeling of the container of the kit or components thereof (i.e., associated with the packaging or sub-packaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

Some or all components of the subject kits may be packaged in suitable packaging to maintain sterility. In many embodiments of the subject kits, the components of the kit are packaged in a kit containment element to make a single, easily handled unit, where the kit containment element, e.g., box or analogous structure, may or may not be an airtight container, e.g., to further preserve the sterility of some or all of the components of the kit.

EXPERIMENTAL

The following examples are put forth so as to provide those of ordinary skill in the art with a complete disclosure and description of how to make and use the present invention, and are not intended to limit the scope of what the inventors regard as their invention. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Treatment of Obesity-Hypoventilation Syndrome (OHS) with Electrical Stimulation of Diaphragm/Chest Wall Muscles A clinical trial is run that compares OHS patients at baseline and after 3 months of treatment with electrical stimulation of diaphragm and chest wall muscles. The inclusion criteria for the patients with OHS are as follows: body mass index>33, failure of dietetic treatment to induce weight loss with persistence of hypercapnic respiratory failure (PCO2>47 mm Hg) for at least 3 months before treatment with electrical stimulation, and refusal of surgical treatment of obesity based either on clinical criteria or by the patients themselves. Patients are excluded if the FEV1/FVC was lower than 0.65 or if the apnea/hypopnea index (AHI) obtained from a complete polysomnographic study was >20 events per hour. Twenty patients are enrolled in the study protocol. All patients receive oxygen therapy for at least 3 months, and they have been clinically stable for at least 3 months before the beginning of treatment. A baseline clinical and pulmonary functional evaluation followed by an overnight polysomnographic study is obtained before treatment. If the sleep study reveals an AHI<20, the patients are then admitted to the hospital to undergo placement of the electrodes and to adjust stimulation settings to provide adequate ventilation with comfort. Once these goals are achieved, the patients are discharged home and followed up for three months. A new clinical and pulmonary function evaluation is performed after three months.

The clinical outcomes (expressed as percentage of the total number of patients reporting the symptom) before and after treatment include the presence of morning headaches, morning drowsiness, sleepiness, dyspnea, and leg edema. Dyspnea is evaluated using the modified Medical Research Council dyspnea scale. The number of patients is counted who scored the two most severe grades of the scale at baseline and after treatment. Sleepiness is defined according to the international classification of sleep disorders. A change in any lower degree of the scale is considered as improvement in sleepiness. All other outcomes are recorded as either present or absent. Pulmonary function test measurements are obtained with the patients in the sifting position and breathing room air. Forced spirometry readings are obtained using a pneumotachographic spirometer. Lung volume and airway resistance are determined using body plethysmography. Arterial blood gases obtained without nasal ventilation in place are processed immediately in a blood gas analyzer. Maximal inspiratory and expiratory muscle pressures are measured from residual volume and total lung capacity, respectively, using a manometer. Sleep studies using a commercially available system are obtained only at baseline to screen out patients with significant sleep apnea syndrome (AHI>20). Sleep duration in every case is >4 hours. During sleep, the following parameters are recorded: electro-oculogram, ECG, electromyogram (submental and anterior tibial), EEG, oronasal flow with a thermistor, thoracic and abdominal movements with inductance plethysmographic bands, and oxygen saturation with a pulse oximeter.

For each patient that qualified for the study and who consented to participate, electrodes are placed at appropriate sites on the diaphragm and chest wall per a proprietary minimally invasive protocol. Following placement, an in-hospital adaptation period for adjustment of setting lasted seven days. The parameters are programmed to achieve the maximal reduction in $PCO_2$, taking into account the patient's ability to tolerate stimulation. The course of treatment lasts three months (ninety days). After treatment with electrical stimulation, statistically significant improvements are noted in pH, $PO_2$, and $PCO_2$ compared to values obtained prior to treatment.

All publications and patents and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A method of treating a subject for obesity-hypoventilation syndrome (OHS), said method comprising:
   providing a subject diagnosed with OHS, wherein the subject has persistence of hypercapnic respiratory failure with a $PCO_2$>47 mmHg for at least three months, a body mass index greater than 33, an apnea-hypopnea index (AHI) measured from a complete polysomnographic study of less than 20 events per hour, and a forced expiratory volume/forced vital capacity ($FEV_1/FVC$ ratio above 0.65; and treating said subject for OHS by applying an electrical stimulus to:

a diaphragm target site, wherein the stimulus enhances diaphragm contraction during expiration and the stimulus enhances diaphragm relaxation during inspiration; and a chest wall target site, wherein the stimulus enhances chest cavity capacity during inspiration and reduces chest cavity capacity during expiration.

2. The method according to claim 1, wherein said method comprises applying the electrical stimulus to said chest wall target site to enhance chest wall contraction.

3. The method according to claim 1, wherein said electrical stimulus is continuous.

4. The method according to claim 1, wherein said electrical stimulus is from an implanted intramuscular electrode adjacent to a point of termination of the corresponding motor nerve supply for the muscle at said target site.

5. The method according to claim 1, wherein said method further comprises synchronizing said electrical stimulus of said at least one target site with said subject's own attempts at breathing.

6. The method according to claim 1, wherein the electrical stimulation of the diaphragm and chest wall target sites is performed to achieve the maximum possible total lung capacity for said subject.

7. The method according to claim 1, wherein said electrical stimulus is applied during expiration to inhibit native electrical stimulation of the diaphragm.

8. The method according to claim 1, wherein said electrical stimulus is applied during expiration to inhibit native electrical stimulation of said subject's chest wall muscles.

9. The method according to claim 1, wherein dietetic treatment has failed to induce weight loss in said subject for at least 3 months.

* * * * *